United States Patent [19]

Kanare

[11] Patent Number: 5,016,629
[45] Date of Patent: May 21, 1991

[54] HOT AND COLD BODY PACK

[76] Inventor: Donald Kanare, 2610 St. Margaret Ct., Alameda, Calif. 94501

[21] Appl. No.: 382,392

[22] Filed: Jul. 20, 1989

[51] Int. Cl.⁵ .............................................. A61F 7/08
[52] U.S. Cl. .................................... 128/402; 383/901
[58] Field of Search ............... 128/379, 380, 402, 403, 128/400, 82.1; 383/901; 62/530; 165/46

[56] References Cited

U.S. PATENT DOCUMENTS

| | | | |
|---|---|---|---|
| 783,827 | 2/1905 | Gasaway et al. | 128/403 |
| 1,910,328 | 5/1933 | Glennan | 128/402 |
| 2,606,005 | 8/1952 | Poux | 165/46 |
| 3,674,034 | 7/1972 | Hardy | 128/400 |
| 3,678,936 | 7/1972 | McCormick | 128/402 |
| 3,736,769 | 6/1973 | Petersen | 128/402 |
| 3,889,684 | 6/1975 | Lebold | 128/402 |
| 4,061,897 | 12/1977 | Thykeson | 128/379 |
| 4,190,054 | 2/1980 | Brennan | 128/402 |
| 4,347,848 | 9/1982 | Hubbard | 128/402 |
| 4,381,025 | 4/1983 | Schooley | 128/402 |
| 4,556,055 | 12/1985 | Bonner | 128/402 |
| 4,585,003 | 4/1986 | Meistrell | 128/402 |
| 4,592,358 | 6/1986 | Westplate | 128/402 |
| 4,676,247 | 6/1987 | Van Cleve | 128/402 |
| 4,753,240 | 6/1988 | Sparks | 128/402 |

*Primary Examiner*—Edward M. Coven
*Assistant Examiner*—M. Graham
*Attorney, Agent, or Firm*—Bielen, Peterson & Lampe

[57] ABSTRACT

A hot or cold body pack utilizing a heat transferring element which includes a bag having a first heat insulative portion and a second heat porous portion. The heat porous portion also mechanically retains a heat transfer element within the bag. The bag includes an opening to retain the heat transfer element. First and second loop members extend along separate dimensions on the outer surface of the bag to permit the straps to hold the bag to a body. Fastener material along an edge of the bag allows it be fastened to another pack.

5 Claims, 2 Drawing Sheets

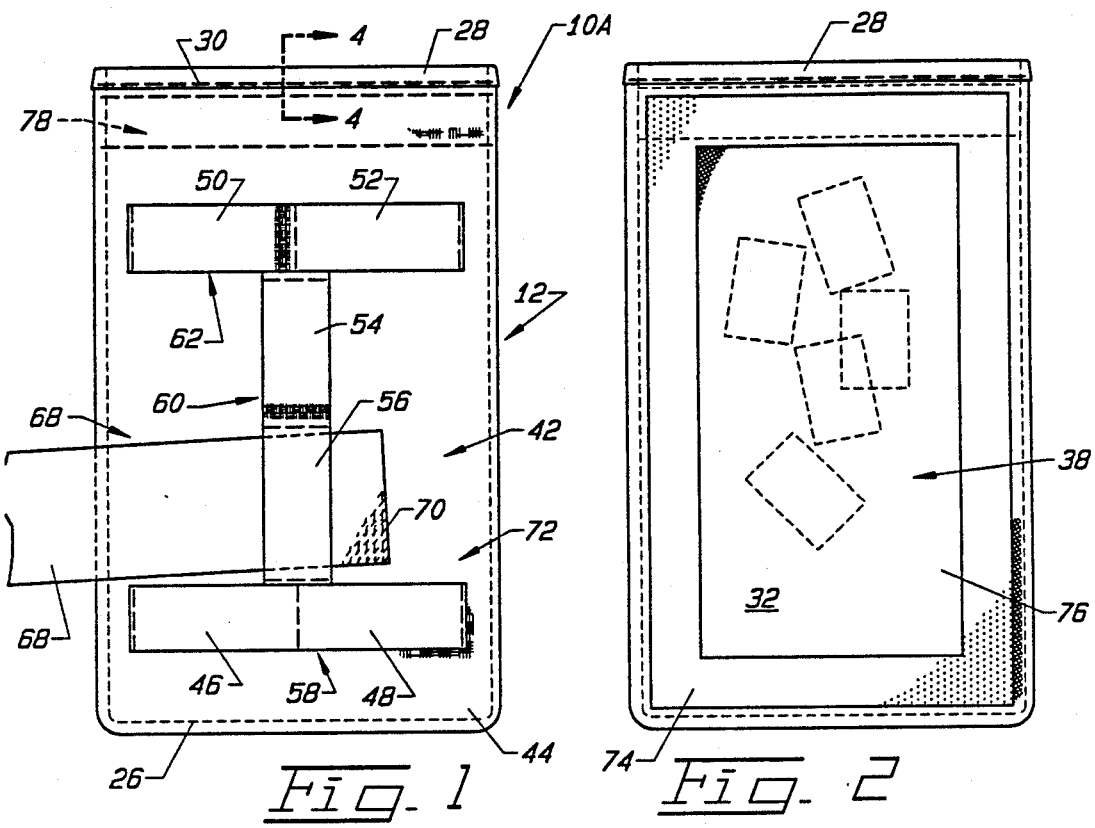
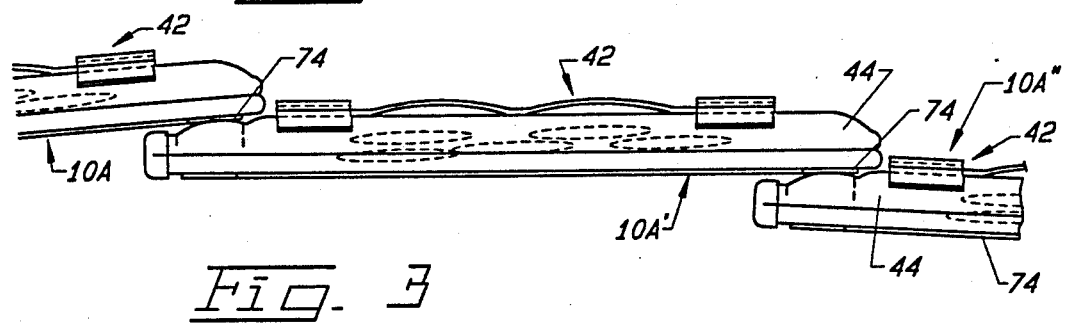
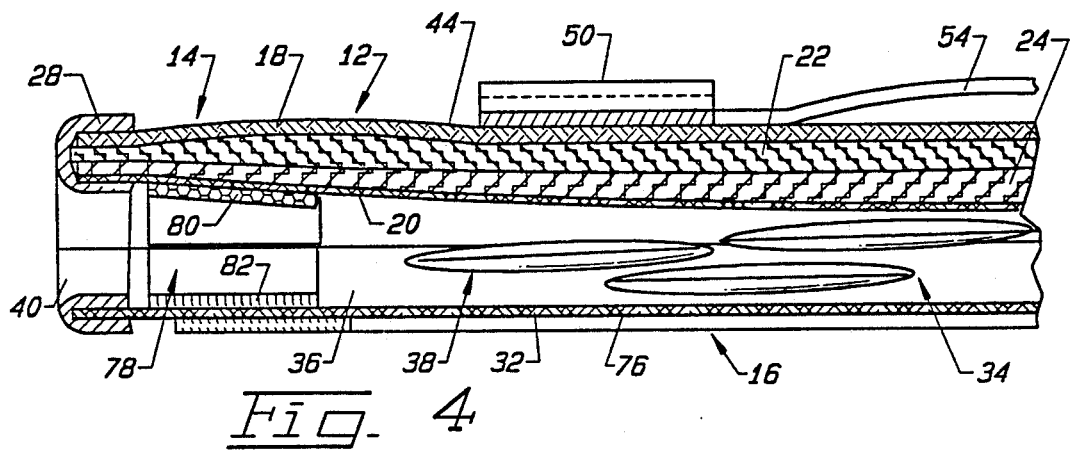

HOT AND COLD BODY PACK

BACKGROUND OF THE INVENTION

The invention relates to a novel body pack which permits the transfer of heat for therapeutic purposes.

It has long been accepted medical practice to apply a cool element to the surface of a body in the vicinity of an injury. In the former case, so called "ice pack" reduces debilitating swelling. On the other hand, a "hot pack" accentuates the healing process. It has often been a problem to securely hold a hot or cold pack to the body for a period of time. Also, adapting a heat transferring pack for securement to multiple portions of the body has long been a problem in the medical field.

Many devices have been proposed which improve on the hot water bottle and ice compress. For example, U.S. Pat. No. 4,381,025 shows a hot or cold pack which wraps around a portion of the body by the use of hook and pile fasteners. U.S. Pat. Nos. 3,678,936, 3,889,684, 4,190,054, and 4,592,358, describe therapeutic hot or cold packs having compartments that are fastened to a body by the use of straps.

U.S. Pat. No. 4,585,003 describes an ice pack which utilizes stretchable foam material and hook and pile connectors to hold the ice pack to the neck region of a body. U.S. Pat. Nos. 4,347,848 and 4,556,055 employ absorbent material within an ice pack to gather condensation which is produced by the ice pack.

U.S. Pat. No. 3,736,769 shows a cooling device which is sandwiched between two flexible walls having different heat transfers rates.

A hot/cold pack which solves the problem encountered in the prior art would be a great advance in the medical field.

SUMMARY OF THE INVENTION

In accordance with the present invention a novel and useful hot/cold body pack is provided.

The body pack of the present invention utilizes a bag having a first heat insulative portion and a second heat porous and mechanically retaining portion. The bag is intended to hold a heat transferring element in the form of a hot source or a cold source. In this regard, the bag possesses an opening to permit entry of the heat transferring element. Such opening may be latched by conventional means such as snaps, hook and pile fasteners, and the like.

The bag includes an outer surface adjacent the first insulative portion which serves as a matrix for a loop member. First loop member may include a plurality of loops extending in multiple directions. The loop member may be attached to the outer surface of the bag or fastened to the bag by other means.

Strap means is also provided for selectively passing through the loop member or any of the plurality of loops associated with the loop member. The strap means may take the form of a rigid or elastic member. Strap means is held to the bag by fasteners such as hook and pile fasteners formed entirely on the strap or formed in conjunction with the outer surface of the bag.

The second portion of the bag may be formed of a mesh layer which would be useful with heat transferring elements that are self contained i.e.: greatly reducing the possibility of moisture emanating from the heat transferring element. On the other hand, the second portion of the bag may be formed of water repellent material where water or condensation may be a problem relative the heat transferring element.

The body pack of the present invention may also include a flap element formed adjacent the second portion of the bag. Such a flap would permit the entry of the portion of the body e.g.: hand, a leg, and the like. Thus, the body portion would be held adjacent to the second portion of the bag and receive the therapeutic benefit of the heat transferring element within the bag.

In addition, a strip of material may be sewn to the second portion on the outer surface of the bag to form a hook and pile fastener with a bag of similar construction. In this manner, multiple bags may be placed in tandem on the body of the user.

It may be apparent that a novel and useful hot/cold body pack has been described.

It is therefore an object of the present invention to provide a hot/cold body pack which is capable of being attached to the body by using multiple strap configurations.

Another object of the present invention is to provide a hot/cold body pack which is capable of being attached to hard-to-reach portions of the body with minimal effort.

A further object of the present invention is to provide a hot/cold body pack which is usable with self contained heat transferring elements.

Yet another object of the present invention is to provide a hot/cold body pack which employs a hook and pile type of fastener which is provided, in part, by the body pack structure itself.

A further object of the present invention is to provide a hot/cold body pack which is washable and not subject to mildew or moisture damage.

A further object of the present invention is to provide a hot/cold body pack which is capable of operating in tandem with body packs of similar construction and dimension.

The invention possesses other objects and advantages especially as concerns particular characteristics and features thereof which will become apparent as the specification continues.

BRIEF DESCRIPTION OF THE DRAWINGS

FIG. 1 is a top plan view of an embodiment of the present invention.

FIG. 2 is a bottom plan view of the embodiment of the present invention depicted in FIG. 1.

FIG. 3 is a broken side elevational view of a plurality of body packs fastened to one another.

FIG. 4 is a sectional view taken along line 4—4 of FIG. 1 showing the layering structure of the embodiment depicted in FIG. 1.

Figure 5:
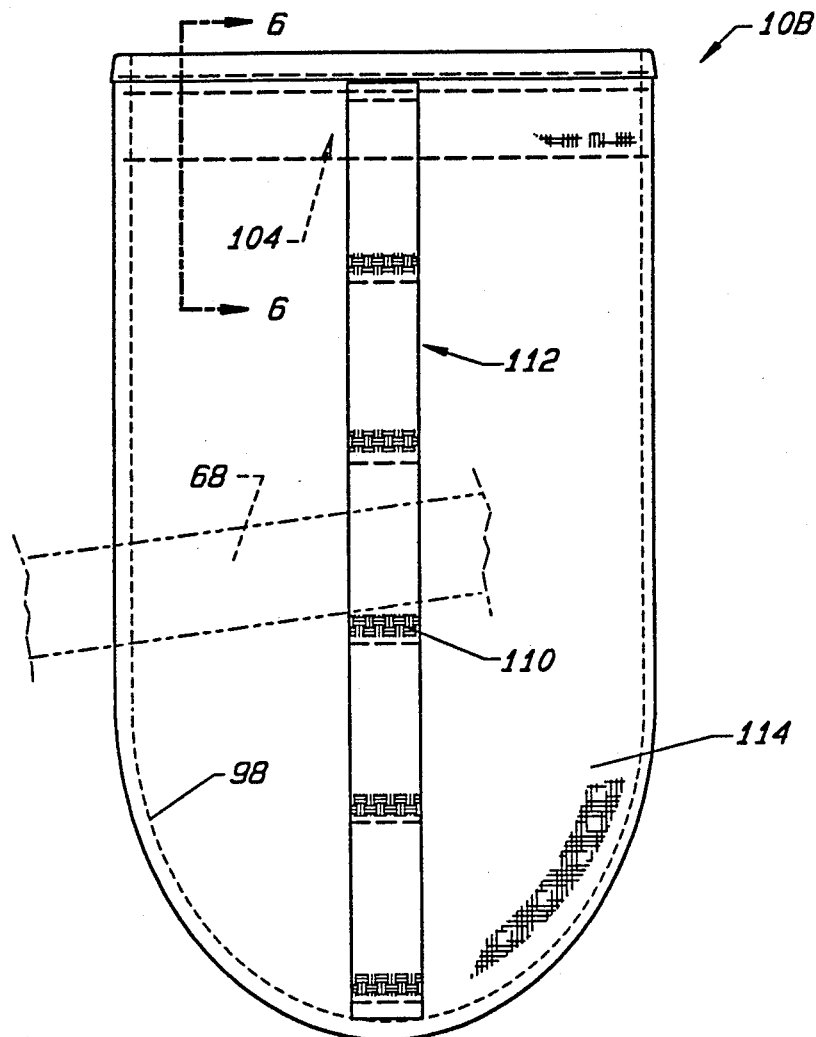
FIG. 5 is a top plan view of another embodiment of the present invention.

For a better understanding of the invention reference is made to the following detailed description of the preferred embodiments which should be referenced to the hereinabove described drawings.

DESCRIPTION OF THE PREFERRED EMBODIMENTS

Various aspects of the present invention will evolve from the following detailed description thereof which should be taken in conjunction with the prior detailed drawings.

The invention is shown, as a whole, in the drawings by reference character 10 with an upper case letter to distinguish embodiments of the same. With reference to FIG. 1, the hot/cold body pack 10A is depicted and includes as one of its elements a bag 12. Bag 12 is formed by a first heat insulative portion 14 and a second heat porous and mechanically retaining portions 16, best shown in FIG. 4.

With reference to first portion 14, it may be observed that layers 18 and 20 enclose insulative layers 22 and 20. Layers 18 and 24 are generally formed of water repellent material such as nylon pack cloth. Layers 18 and 20 are held to each other by sew line 26. Selvage member 28 is sewn to layers 18, 20, 22 and 24 along sew line 30, FIG. 1. Of course, selvage member 28 may be affixed to first portion 14 of bag 12 by other means such as gluing, sonic welding, and the like.

Bag 12 second portion 16 includes a layer 32 which permits the passage of heat from heat transfer element 34 within chamber 36 of bag 12. Layer 32 may be an open mesh or a rather thin water repellent layer such as nylon pack cloth. In any case, the transfer of heat from heat transfer element 34 is biased through layer 32 by the action of the insulative qualities of first portion 14 of bag 12. Heat transfer element 34 is shown as a plurality of self contained packets 38 which may be cold or hot. Packets 38 are of a slim configuration to fit easily within opening 40 of bag 12. It should be noted that selvage member 28 encompasses layer 32. Also, sew line 26 holds layer 32 to layers 18, 20, 22, and 24 of first portion 14 to form bag 12. Thus, a cooling or heating originating with heat transfer element 34 would reach a body portion placed adjacent layer 32.

Body pack 10A, FIGS. 1-4 also possesses a loop member 42 which extends from the outer surface 44 of layer 18. As depicted in the drawings, loop member 42 includes loops 46, 48, 50, and 52, as well as loops 54 and 56. Loop member 42 is formed by sewing webbing strips 58, 60, and 62 to layer 18. It should be noted that strip 60 is angularily oriented relative to strips 58 and 62. Thus, loops 46, 48, 50 and 42 are angularly oriented relative to loops 54 and 56. Strap means 68 may slip through any of the loops, but is shown passing through loop 56 of strip 60. Layer 18 may be formed of a pile material known as Velvet Loop manufactured by Gilford Mills of New York City, N.Y. Strap means 68 may include a hook portion 70 which engages and holds to pile surface 44 of layer 18. Thus strap 68 may be fastened at any portion of surface 44 of layer 18 while being guided by loop member 42. It should be noted that the other end of strap means 68 may also include such hook material (not shown) such as hook portion 70. In other words, surface 44 and hook portion 70 of strap 68 form a hook and pile connector 72. Further, the other end of strap means 68 may be formed with a pile material to form a hook and pile connector known as a Velcro fastener.

Turning to FIG. 2 it may be observed that a strip of hook material 74 is fastened by sewing, or otherwise, to the periphery of surface 76 of layer 32. Focusing on FIG. 3, it may be observed that strip 74 of pack 10A engages surface 44 of identical pack 10A'. Likewise, strip 74 of body pack 10A' engages surface 44 of identical body pack 10A''. Thus, the embodiment depicted in FIGS. 1-4 may be linked in sort of a chain to cover larger portions of the body.

It should be noted that means 78 for latching or closing chamber 36 of bag 12 is also shown on FIG. 4. Latching means 78 is depicted in the form of hook and pile (Velcro) strips 80 and 82 fastened to layers 20 and 32.

Figure 6:
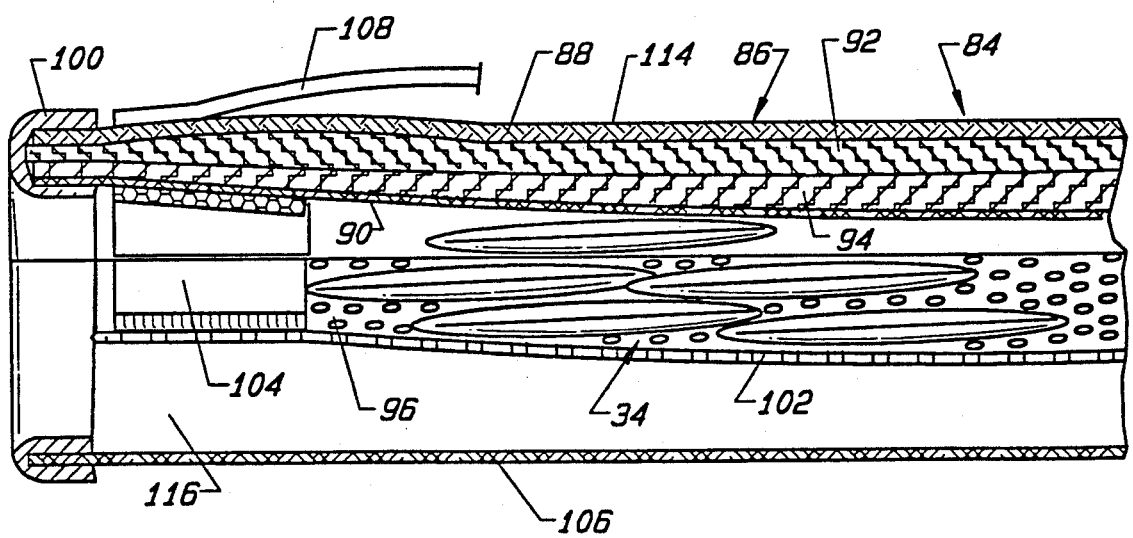
FIG. 6 is a sectional view taken along line 6—6 of FIG. 5 showing the layering structure of another embodiment of the present invention.

Turning to FIGS. 5 and 6, another embodiment 10B of the invention is illustrated. Body pack 10B is in the form of a mit and includes a bag 84 having a first heat insulative layer 86 formed of water repellent layers 88 and 90 and insulation layers 92 and 94. Again, a chamber 96 is formed to contain heat transfer element 34. Sew line 98 aids in the formation of bag 84. Second portion 102 of bag 84 is shown as a mesh, although a water repellent material may also be used therefor. Thus, second portion 102 is heat porous and mechanically retains heat transfer element 34. Velcro closure means 104 permits chamber 96 to be closed. Selvage member 100 also holds a flap 106. Flap 106 may be formed of water repellent material such a nylon pack cloth and is held to mit 10B by sew line 98, FIG. 5. A loop member 108 consist of a strip of webbing 110 which has been selectively fastened to layer 88 to form a plurality of loops 12. As in embodiment 10A, strap means 68 may be employed to hold mit 10B to a body. Surface 114 of layer 88 may comprise a Velvet Loop pile material which is caught by hook material found on strap means 68.

In operation, the user of embodiment 10A fills bag 12 with heat transfer element 34 which may be in the form of self-contained hot or cold packets. Opening 40 to bag 12 is then closed by latching means 78 and pack 10A is placed to the portion of the body requiring the application of heat or cold. Strap means 68 is placed through loop member 42 in the desired direction or directions, wrapped around the appropriate body part, and fastened to surface 44 of layer 18 to itself, to complete the holding process. The body pack 10A may be linked or connected together to form a larger area of heat transfer to the body. Strap means 68 may be used in this regard in conjunction with any of the loop members 42.

In the embodiment 10B illustrated in FIGS. 5 and 6, the user fills bag 84 with heat element 34 and employs Velcro closure 104 to keep the same within chamber 96. The user then slips a body part, such as a hand, within another chamber 116 formed by flap 106. Strap means such as strap means 68 may be employed with loop member 108 to securely hold the mit 10B to the particular body portions such as a hand or foot. Mesh layer 102 would permit any condensation to pass into chamber 116. However, water repellent layer 106 would prevent passage of moisture to the exterior of mit 10B.

While in the foregoing embodiments of the invention have been set forth in considerable detail for the purpose of making a complete disclosure of the invention it may be apparent to those of skill in the art that numerous changes may be made in such details without departing from the spirit and principles of the invention.

What is claimed is:

1. A hot or cold body pack utilizing a heat transferring element; comprising:
   a. a bag including a first heat insulative portion and a second heat porous and mechanically retaining portion, said bag further including an opening thereto to permit entry of the heat transferring element, said bag having an outer surface adjacent said first insulative portion;
   b. a first loop extending along a first dimension of said outer surface of said bag;

c. a second loop extending along a second dimension of said outer surface of said bag said second dimension being angularly oriented relative to said first dimension;

d. strap means for selectively passing through said first and second loops;

e. means for holding said strap means relative to said bag, said strap holding means including substantially said entire outer surface of said bag forming a pile fastener for connecting with hook material located on said strap means; and f. a strip of hook material connected to the outer surface of said bag along an edge of said second heat porous and mechanically retaining portion of said bag, said strip allowing for connection of said pack to a second pack.

2. The body pack of claim 1 in which said second heat porous and mechanically retaining portion of said bag comprises a mesh layer.

3. The body pack of claim 1 in which said second heat porous and mechanically retaining portion of said bag comprises a water repellent layer.

4. The body pack of claim 1 in which said bag opening includes means for latching said opening.

5. The body pack of claim 1 in which said first insulative portion includes an insulation member enclosed by a water repellent member.

* * * * *